July 18, 1950 W. L. SPANDIKOW Plant Pat. 964
ROSE PLANT
Filed March 31, 1949
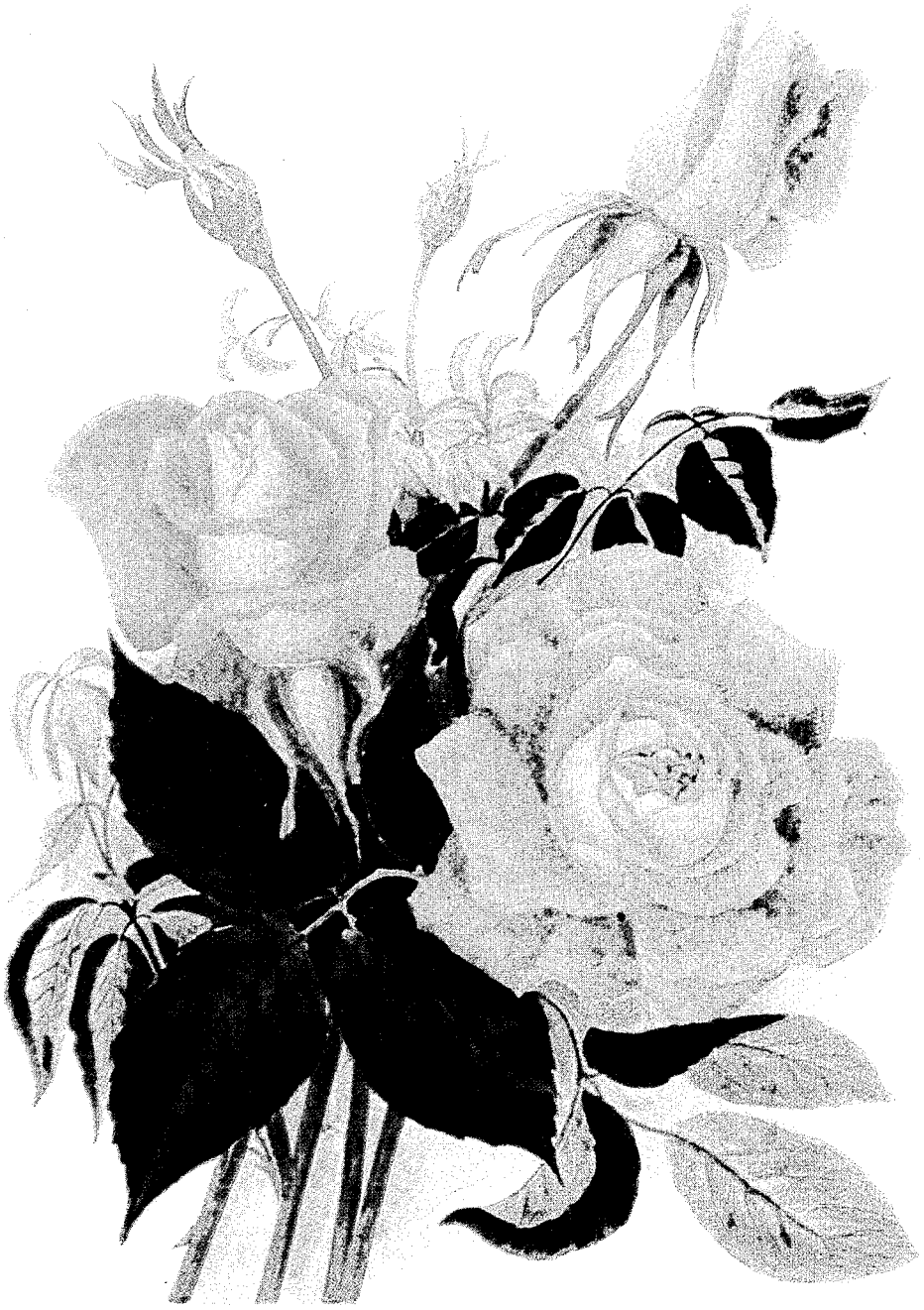
WITNESS
Addison J. Avery
INVENTOR
WILLIAM L SPANDIKOW,
By Rummler Rummler & Snow,
ATTYS.

Patented July 18, 1950

Plant Pat. 964

UNITED STATES PATENT OFFICE

964

ROSE PLANT

William L. Spandikow, Melrose Park, Ill., assignor to William Spandikow & Sons Co., a corporation of Illinois Application March 31, 1949, Serial No. 84,540

1 Claim. (Cl. 47—61)

This discovery relates to a new and distinct variety of rose plant which originated as a sport of the well-known hybrid tea variety "Better Times" (Plant Patent #23). My new variety was discovered at Melrose Park, Cook County, Illinois, in January 1947; at which place it has been asexually reproduced by grafting, and its characteristics appear to be permanently fixed.

The main object of this discovery was to establish the warm and brilliant Tyrian Rose Purple color of the bloom and other features of superiority over the parent variety. Such superior features include its more prolific growing habit; a distinct difference in the opening of the flower—nearly all petals open and develop at the same time; the color of the bloom is darker and richer; it is more persistent in producing its richly colored blooms when conditions are not favorable, and its blooms are exactly alike and uniform in color, showing no variation, when bunched in large lots cut at random.

This variety resembles its parent variety as regards the height of the plant, the productivity of blooms and number of petals in the flowers.

This new variety is particularly well suited for commercial production of plants for greenhouse and outdoor raising of cut flowers. The brilliancy and uniformity of the color of the blooms is a dominant commercial factor. The stems are long, sturdy and straight, being smooth and without thorns or prickles in the upper four or five internodes. The foliage is abundant and the leaves are characterized by being distinctly long. New shoots are reddish brown in color and gradually turn to green from the bottom up to the tip of the stem.

The accompanying illustration shows in full color specimens of this new variety in various stages of development of its blooms and foliage.

A more detailed description of the identifying features of the plant is as follows:

Parentage: Sport of "Better Times."

Plant:

*Form.*—Bush.

*Growth.*—Vigorous and hardy.

*Texture.*—Woody.

Foliage: Abundant with leaves mainly compound in groups of five, but changing to groups of three and a single leaf toward tip of stem.

*Size of leaf.*—3⅜ x 1¾ inches.

*Shape.*—Ovate-acuminate.

*Texture.*—Leathery. Upper side: glossy and smooth; under side: velvety.

*Color of mature leaf.*—Upper side, dark green; lower side, pinkish grey green.

*Petioles.*—4 inches long.

*Thorns.*—Occurring only in lower part of stem. Color—reddish-brown. Size—$\frac{3}{16}$ inch.

*Disease resistance.*—Highly resistant to black spot. More so than parent.

*Lasting quality.*—Better than parent plant both on plant and as a cut flower.

Stems:

*Length.*—Without pinching, 30 to 40 inches.

*Strong.*—Very.

*Internodes.*—Average length, 3 inches.

*Shoots.*—Many—depends on weather conditions. Red-brown in color.

Flower: Blooming habit—continuous and profuse.

Bud:

*Size.*—1⅞ x ¾ inches.

*Form.*—Long and pointed.

*Sepals.*—Hood over bud. As bud develops they curl back.

*Calyx.*—Shape—same as parent.

*Peduncle.*—Smooth and heavier than parent.

Bloom: 2 inches deep by 4 inches in diameter.

*Borne.*—Singly.

*Shape.*—High center. Petals about equal length.

*Petalage.*—Somewhat variable with an average of about 34.

*Size of petal.*—1¾ x 1¾ inches.

*Form of petal.*—Practically round with one point at apex and with slightly ruffled side margins that are rolled back around cupped central area.

*Texture.*—Firm.

*Appearance.*—Outside of petal, satiny. Inside of petal, velvety.

*Discoloration.*—None whatever.

*Persistent (hang on and dry).*—Yes.

Genital organs: Completely covered.

More precise designation of colors in various parts of the plant are indicated in the following chart in which certain colors of the natural plant are compared with identifying indicia of British Horticultural Chart and others are identified by reference to Maerz & Paul.

| Section | Br. Horticultural | Maerz & Paul | | |
|---|---|---|---|---|
| | | Plate | Ltr. | No. |
| Outside of back of petal | Tyrian Rose, o24/1. | | | |
| Face of petals (rich crimson) | | 3 | L | 6 |
| Face of petals with purple red shadows. | Tyrian-Purple, 727. | | | |
| Main face of mature leaf | | 24 | H | 5 |
| Back of nearly mature leaf | | 21 | C | 3 |
| Overcast with purple | | 46 | D | 1 |
| Small new foliage | | 6 | U | 10 |
| Larger new foliage | | 56 | L | 1 |
| Stem | | 21 | L | 6 |

Having thus disclosed the invention, I claim:

A new and distinct variety of hybrid tea rose plant, substantially as described and illustrated, characterized by the uniformity of color and shape of its blooms having nearly round petals with pointed apex and ruffled edges on their curled margins, and by its sturdy long smooth stems with distinctive foliage.

WILLIAM L. SPANDIKOW.

No references cited.